(12) United States Patent
Law et al.

(10) Patent No.: US 7,342,129 B2
(45) Date of Patent: Mar. 11, 2008

(54) PROCESS FOR THE PRODUCTION OF ACETIC ACID

(75) Inventors: David John Law, Beverley (GB); Andrew David Poole, South Cave (GB); Stephen James Smith, Cottingham (GB); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 10/516,623

(22) PCT Filed: May 29, 2003

(86) PCT No.: PCT/GB03/02347

§ 371 (c)(1),
(2), (4) Date: Dec. 3, 2004

(87) PCT Pub. No.: WO03/106396

PCT Pub. Date: Dec. 24, 2003

(65) Prior Publication Data

US 2005/0176996 A1      Aug. 11, 2005

(30) Foreign Application Priority Data

Jun. 12, 2002   (GB)   ................................. 0213485.6

(51) Int. Cl.
*C07C 51/12*       (2006.01)

(52) U.S. Cl. ...................................................... 562/519
(58) Field of Classification Search .................... None
See application file for complete search history.

(56) References Cited

U.S. PATENT DOCUMENTS 5,877,348 A * 3/1999 Ditzel et al. ................. 562/519
6,211,405 B1 * 4/2001 Cheung et al. ............. 562/519

FOREIGN PATENT DOCUMENTS

EP      0 849 248 A     6/1998
EP      0 849 250 A     6/1998

* cited by examiner

Primary Examiner—Paul A. Zucker
(74) Attorney, Agent, or Firm—Nixon & Vanderhye (57) ABSTRACT

A process for the production of acetic acid by carbonylating methanol and/or a reactive derivative thereof with carbon monoxide in a carbonylation reactor containing a liquid reaction composition comprising an iridium carbonylation catalyst, methyl iodide co-catalyst, a finite concentration of water, acetic acid, methyl acetate, at least one promoter selected from ruthenium, osmium and rhenium and a stabilising compound selected from the group consisting of alkali metal iodides, alkaline earth metal iodides, metal complexes capable of generating I−, salts capable of generating I−, and mixtures of two or more thereof wherein the molar ratio of promoter to iridium is greater than 2:1, and the molar ratio of stabilising compound to iridium is in the range [greater than 0 to 5]:1.

22 Claims, 2 Drawing Sheets

PROCESS FOR THE PRODUCTION OF ACETIC ACID

This application is the U.S. National Phase of International Application PCT/GB03/02347, filed 29 May 2003, which designated the U.S. PCT/GB03/02347 claims priority to British Application No. 0213485.6 filed 12 Jun. 2002. The entire content of these applications are incorporated herein by reference.

The present invention relates to a process for the production of acetic acid and in particular to a process for the porduction of acetic acid by carbonylation in the presence of an iridium catalyst, methyl iodide co-catalyst and a promoter.

BACKGROUND OF THE INVENTION

The production of acetic acid by the carbonylation of methanol in the presence of an iridium catalyst and a promoter such as ruthenium is described, for example, in EP-A-0752406, EP-A-0849248, EP-A-0849249, and EP-A-1002785.

WO-A-95/31426 discloses a process for the production of carboxylic acids or their esters having (n+1) carbon atoms by the liquid phase reaction of carbon monoxide with at least one alcohol having (n) carbon atoms in the presence of a catalytic system based on a compound of iridium and a halogen co-catalyst. The process is characterised by maintaining in the reaction medium water in a volume between greater than 0 and 10%, typically between 0.5 and 8%, preferably between 2 and 8%; the ester corresponding to the carboxylic acid and the alcohol in a volume varying between 2 and 40%; and iodides in soluble form of such a nature that the atomic ratio of the iodides to iridium is between greater than 0 and 10, typically between greater than 0 and 3, preferably between greater than 0 and 1.5. The volume of halogen co-catalyst in the reaction medium is between greater than 0 and 10%; typically between 0.5 and 8%, and preferably between 1 and 6%. Suitable iodides include alkaline earth metal and alkali metal iodides, and specifically lithium iodide. The process of WO-A-95/31426 is otherwise unpromoted.

EP-A-0643034 describes a process for the carbonylation of methanol and/or a reactive derivative thereof in the presence of acetic acid, an iridium catalyst, methyl iodide, at least a finite concentration of water, methyl acetate and a promoter selected from ruthenium and osmium. In EP-A-0643034 it is said that ionic contaminants such as, for example, (a) corrosion metals, particularly nickel, iron and chromium and (b) phosphines or nitrogen-containing compounds or ligands which may quaternise in situ should be kept to a minimum in the liquid reaction composition as these will have an adverse effect on the reaction by generating I- in the liquid reaction composition which has an adverse effect on the reaction rate. Similarly, it is said, contaminants such as alkali metal iodides, for example lithium iodide, should be kept to a minimum.

SUMMARY OF THE INVENTION

In WO-A-96/23757 which is directed to the preparation of iridium carboxylates and their use in inter alia carbonylation reactions, the use of promoters not being mentioned, it is stated in contrast to WO-A-95/314326 that alkaline or alkaline earth ions are preferably eliminated, since their presence may have a harmful influence on the kinetics and selectivity of subsequent reactions in which the iridium carboxylate will e used as a catalyst.

Under certain operating conditions, it has been observed that a catalyst system (iridium and ruthenium promoter) may precipitate. An effective method of ensuring that catalyst and promoter losses are reduced is to add a stabilising compound which prevents or at least mitigates precipitation of the catalyst system from the process streams. This is particularly important in the acetic acid product recovery streams since, at some point after reaction, the level of carbon monoxide pressure is reduced and hence the probability of some catalyst system precipitating from solution is increased.

Precipitation of the catalyst system has also been observed to occur when the process is operated using relatively high concentrations of promoter, such as a molar ratio of Ru to Ir of at least 2:1. Similarly, precipitation may also be a problem for other promoter species such as those containing osmium or rhenium.

Thus, there remains a need for an improved iridium-catalysed promoted carbonylation process in which catalyst and promoter losses are prevented or retarded.

The present invention solves the technical problem defined above by using low concentrations of certain selected iodides. These iodides reduce the generation of insoluble or sparingly soluble catalyst system species such as ruthenium containing complexes. The use of low concentrations of the iodides selected also provide the additional advantage that catalyst system stability may be improved without incurring a significant decrease in the carbonylation rate. In addition, use of the stabilising compound allows the use of reduced levels of carbon monoxide, particularly in a second reaction zone and/or acetic acid product recovery section, and hence allows economic benefits to be achieved.

Advantageously, low concentrations of the selected iodides may be used to reduce the level of catalyst system precipitate after it has been formed, i.e aid resolubilisation of the formed precipitate.

Accordingly, the present invention also provides a process for the production of acetic acid by carbonylating methanol and/or a reactive derivative thereof with carbon monoxide in a carbonylation reaction zone containing a liquid reaction composition comprising an iridium carbonylation catalyst, methyl iodide co-catalyst, a finite concentration of water, acetic acid, methyl acetate, at least one promoter selected from ruthenium, osmium and rhenium and a stabilising compound selected from the group consisting of alkali metal iodides, alkaline earth metal iodides, metal complexes capable of generating I-, salts capable of generating I-, and mixtures of two or more thereof wherein the molar ratio of promoter to iridium is greater than 2:1, and the molar ratio of stabilising compound to iridium is in the range [greater than 0 to 5]:1.

The present invention also provides for the use of a compound selected from the group consisting of alkali metal iodides, alkaline earth metal iodides, metal complexes capable of generating I-, salts capable of generating I-, and mixtures of two or more thereof to stabilise the catalyst and/or promoter under reduced levels of carbon monoxide in a process for the production of acetic acid by carbonylating methanol and/or a reactive derivative thereof with carbon monoxide in a carbonylation reaction zone containing a liquid reaction composition comprising an iridium carbonylation catalyst, methyl iodide co-catalyst, a finite concentration of water, acetic acid, methyl acetate and at least one promoter selected from ruthenium, osmium and rhenium.

The present invention further provides for the use of a compound selected from the group consisting of alkali metal iodides, alkaline earth metal iodides, metal complexes capable of generating I-, salts capable of generating I-, and mixtures of two or more thereof to stabilise the catalyst and/or promoter under reduced levels of carbon monoxide in a process for the production of acetic acid by carbonylating methanol and/or a reactive derivative thereof with carbon monoxide in a carbonylation reaction zone containing a liquid reaction composition comprising an iridium carbonylation catalyst, methyl iodide co-catalyst, a finite concentration of water, acetic acid, methyl acetate, at least one promoter selected from ruthenium, osmium and rhenium and wherein the molar ratio of said compound to iridium is in the range [greater than 0 to 5]:1.

The reaction zone may comprise a conventional liquid-phase carbonylation reaction zone. The pressure of the carbonylation reaction in the first reaction zone is suitably in the range 15 to 200 barg, preferably 15 to 100 barg, more preferably 15 to 50 barg and yet more preferably 18 to 35 barg. The temperature of the carbonylation reaction in the first reaction zone is suitably in the range 100 to 300° C., preferably in the range 150 to 220° C.

Preferably, two reaction zones are used, the first and second reaction zones being maintained in separate reaction vessels with means for withdrawing from the first reaction vessel and passing to the second reaction vessel liquid reaction composition from the first reaction vessel with dissolved and/or entrained carbon monoxide. Such a separate second reaction vessel may comprise a section of pipe between the first reaction vessel and a liquid reaction composition flashing valve. Preferably the pipe is liquid full. Typically the pipe's length to diameter ratio may be about 12:1, though length to diameter ratios both higher and lower than this may be employed.

Typically, at least a portion of the liquid reaction composition together with dissolved and/or entrained carbon monoxide is withdrawn from the first reaction zone and at least a portion of the withdrawn liquid and dissolved and/or entrained carbon monoxide passed to a second reaction zone. Preferably substantially all the liquid reaction composition together with dissolved and/or entrained carbon monoxide withdrawn from the first reaction zone is passed to the second reaction zone.

The second reaction zone may be operated at a reaction temperature in the range 100 to 300° C., preferably in the range 150 to 230° C. The second reaction zone may be operated at a temperature higher than the first reaction zone, typically up to 20° C. higher. The second reaction zone may be operated at a reaction pressure in the range 10 to 200 barg, preferably in the range 15 to 100 barg. Preferably, the reaction pressure in the second reaction zone is equal to or less than the reaction pressure in the first reaction zone. The residence time of liquid reaction composition in the second reaction zone is suitably in the range 5 to 300 seconds, preferably 10 to 100 seconds.

The carbon monoxide reactant for the carbonylation reactions may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 bar partial pressure, as its presence may result in the formation of hydrogenation products. The partial pressure of carbon monoxide in the first and second reaction zones is suitably independently in the range 1 to 70 bar, preferably 1 to 35 bar and more preferably 1 to 15 bar.

There may be introduced to the second reaction zone carbon monoxide in addition to that introduced to the second reaction zone as dissolved and/or entrained carbon monoxide. Such additional carbon monoxide may be co-joined with the first liquid reaction composition prior to introduction to the second reaction zone and/or may be fed separately to one or more locations within the second reaction zone. Such additional carbon monoxide may contain impurities, such as for example $H_2$, $N_2$, $CO_2$ and $CH_4$. The additional carbon monoxide may be comprised of high pressure off-gas from the first reaction zone which could advantageously allow the first reaction zone to be operated at a higher CO pressure with the resulting higher flow of carbon monoxide being fed to the second reaction zone. Additionally it could eliminate the requirement for a high pressure off-gas treatment.

The additional carbon monoxide may also be comprised of another carbon monoxide-containing gas stream such as for example a carbon monoxide-rich stream from another plant.

Preferably greater than 10%, more preferably greater than 25%, even more preferably greater than 50%, for example at least 95%, of the dissolved and/or entrained carbon monoxide in the withdrawn reaction composition from the first reaction zone is consumed in the second reaction zone.

In the process of the present invention, suitable reactive derivatives of methanol include methyl acetate, dimethyl ether and methyl iodide. A mixture of methanol and reactive derivatives thereof may be used as reactants in the process of the present invention. Water is required as co-reactant for ether or ester reactants Preferably, methanol and/or methyl acetate are used as reactants.

At least some of the methanol and/or reactive derivative thereof will be converted to, and hence present as, methyl acetate in the liquid reaction composition by reaction with the carboxylic acid product or solvent. Preferably, the concentrations of methyl acetate in the liquid reaction compositions in the first and second reaction zones are independently in the range 1 to 70% by weight, more preferably 2 to 50% by weight, most preferably 3 to 35% by weight Water may be formed in situ in the liquid reaction compositions, for example, by the esterification reaction between methanol reactant and acetic acid product. Water may be introduced independently to the first and second carbonylation reaction zones together with or separately from other components of the liquid reaction compositions. Water may be separated from other components of reaction compositions withdrawn from the reaction zones and maybe recycled in controlled amounts to maintain the required concentration of water in the liquid reaction compositions. Preferably, the concentrations of water in the liquid reaction compositions in the first and second reaction zones are independently in the range 0.1 to 20% by weight, more preferably 1 to 15% by weight, yet more preferably 1 to 10% by weight.

To maximise catalyst system stability during the acetic acid product recovery, the concentration of water in process streams containing catalyst system for recycle to the carbonylation reaction zones is preferably maintained at a concentration of at least 0.5% by weight.

Preferably, the concentration of methyl iodide co-catalyst in the liquid carbonylation reaction compositions in the first and second reaction zones is independently in the range 1 to 20% by weight, preferably 2 to 16% by weight The iridium catalyst in the liquid reaction compositions in the first and second reaction zones may comprise any iridium-containing compound which is soluble in the liquid reaction compositions. The iridium catalyst may be added to the liquid reaction compositions in any suitable form which dissolves in the liquid reaction compositions or is convertible to a soluble form. Preferably the iridium may be used as a chloride free compound such as acetates which are soluble in one or more of the liquid reaction composition components, for example water and/or acetic acid and so may be added to the reaction as solutions therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^{30}$, $[Ir(CO)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $H_2[IrCl_6]$, preferably free complexes of iridium such as acetates, oxalates and acetoacetates.

Preferably, the concentration of the iridium catalyst in the liquid reaction compositions of the first and second reaction zones is independently in the range 100 to 6000 ppm by weight of iridium.

The liquid reaction compositions in the first and second reaction zones additionally comprises one or more promoters. Suitable promoters are selected from ruthenium, osmium and rhenium, and are more preferably selected from ruthenium and osmium. Ruthenium is the most preferred promoter. The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form.

Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]$—H+, $[Ru(CO)_2I_2]_n$, $[Ru(CO)_4I_2]$, $[Ru(CO)_3I_2]_2$, tetra(aceto)chlororuthenium(II,III), ruthenium (III) acetate, ruthenium (III) propionate, ruthenium (III) butyrate, ruthenium pentacarbonyl, triruthenium-dodecacarbonyl and mixed ruthenium halocarbonyls such as dichlorotricarbonylruthenium (II) dimer, dibromotricarbonylruthenium (II) dimer, and other organoruthenium complexes such as tetrachlorobis (4-cymene)diruthenium(II), tetrachlorobis(benzene)diruthenium(II), dichloro(cycloocta-1',5diene) ruthenium (II) polymer and tris(acetylacetonate) ruthenium (III).

Examples of suitable osmium-containing compounds which may be used as sources of promoter include osmium (III) chloride hydrate and anhydrous, osmium metal, osmium tetraoxide, triosmiumdodecacarbonyl, $[Os(CO)_4I_2]$, $[Os(CO)_3I_2]_2$, $[Os(CO)_3I_3]$—H+, pentachloro-μ-nitrodiosmium and mixed osmium halocarbonyls such as tricarbonyldichloroosmium (II) dimer and other organoosmium complexes.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.xH_2O$, $[Re(CO)_4I]_2$, $Re(CO)_4I_2]^-H^+$ and $ReCl_5.yH_2O$.

Preferably, the promoter is present in an effective amount up to the limit of its solubility in the liquid reaction composition and/or any liquid process streams recycled to the carbonylation reactor from the acetic acid recovery stage. The promoter is suitably present in the liquid reaction composition at a molar ratio of promoter to iridium of [greater than 2 to 15]:1, preferably [greater than 2 to 10]:1, more preferably [4 to 10]:1. A suitable promoter concentration is less than 8000 ppm, such as 400 to 7000 ppm.

The liquid reaction compositions also comprise a stabilising compound selected from alkali metal iodides, alkaline earth metal iodides, metal complexes capable of generating I-, salts capable of generating I-, and mixtures of two or more thereof. Suitable alkali metal iodides include lithium iodide, sodium iodide and potassium iodide. Suitable alkaline earth metal iodides include calcium iodide. Suitable metal complexes capable of generating I- include complexes of the lanthanide metals, for example, samarium and gadolinium, cerium, and other metals such as molybdenum, nickel; iron, aluminium and chromium. Salts capable of generating I- include, for example, acetates which are capable of conversion in-situ to I- typically, alkali metal and alkaline earth metal acetates such as sodium acetate and lithium acetate and organic salts, such as quaternary ammonium iodides and phosphonium iodides, which may be added as such. A preferred stabilising compound is lithium iodide.

Suitably, the amount of stabilising compound used is such that it is effective in providing an increase in the solubility of the catalyst system and preferably, does not significantly decrease the carbonylation reaction rate.

The amount of stabilising compound introduced to the liquid reaction compositions should be selected to take account of the presence of I- from other sources because it is believed that an excessive amount of I- in the liquid reaction compositions may be detrimental. The optimum ratio of the stabilising compound is selected depending on the nature of the chosen iodide compound, the counter ion, the degree of dissociation in the carbonylation medium and the molar ratio of promoter:iridium used.

It has been found that a molar ratio of stabilising compound:iridium in the range [greater than 0 to 5]:1 is effective in providing increased stability of the catalyst system and, in particular, where the molar ratio of promoter to iridium is greater than 2:1, for example at least 3:1 such as in the range [4 to 12]:1.

Preferably, where the molar ratio of promoter to iridium is greater than 2:1, such as in the range [greater than 2 to 15]:1, for example, in the range [greater than 2 to 12]:1 or [greater than 2 to 5]:1, the molar ratio of stabilising compound to iridium is in the range [0.05 to 3]:1, such as [0.05 to 1.5]:1.

Suitably, where the molar ratio of promoter to iridium is 4:1 or greater, such as in the range [4 to 10]:1, the molar ratio of stabilising compound:iridium is in the range [0.05 to 5]:1, for example, [0.15 to 3]:1, such as [0.15 to 2.5]:1 Suitably, for a molar ratio of promoter to iridium of at least 5:1, such as in the range [greater than 5 to 12]:1, for example, [6 to 12]:1, the molar ratio of stabilising compound to iridium is preferably in the range [0.05 to 5]:1, for example [0.15:3]:1, such as [0.15 to 2.5]:1 or [0.15 to 2]:1.

Preferably, the promoter is ruthenium and the stabilising compound is selected from lithium iodide, sodium iodide, potassium iodide and quaternary ammonium and phosphonium iodides, most preferably lithium iodide or sodium iodide. Where these stabilising compounds are used and the ruthenium:iridium molar ratio is in the range [2 to 5]:1, the molar ratio of the stabilising compound to iridium is preferably [0.05 to 1.5]:1. Where the ruthenium to iridium molar ratio of is about 4:1 or greater, such as [4 to 10]:1, the molar ratio of stabilising compound to iridium may suitably be in the range [0.05 to 1.5]:1, such as in the range [0.15 to 1.5]:1. Where the molar ratio of ruthenium:iridium is greater than 5:1, such as [6 to 12]:1, preferably, the molar ratio of stabilising compound to iridium is [0.05 to 3]:1, such as [0.05 to 2]:1.

The stabilising compound may be introduced into the reaction zone(s) at any stage during the carbonylation reaction. The stabilising compound may be introduced directly into a reaction zone, for example, via a reactant feed stream or it may be introduced indirectly into a reaction zone, for example via a recycle stream such as a catalyst recycle stream.

The present invention also provides for the use of a compound selected from the group consisting of alkali metal iodides, alkaline earth metal iodides, metal complexes capable of generating I-, salts capable of generating I-, and mixtures of two or more thereof to solubilise a catalyst system precipitate, the catalyst system precipitate having been formed under reduced levels of carbon monoxide in a process for the production of acetic acid by carbonylating methanol and/or a reactive derivative thereof with carbon monoxide in a carbonylation reaction zone containing a liquid reaction composition comprising an iridium carbonylation catalyst, methyl iodide co-catalyst, a finite concentration of water, acetic acid, methyl acetate and at least one promoter selected from ruthenium, osmium and rhenium.

Catalyst system precipitate generally forms when process streams are subjected to reduced concentrations of carbon monoxide such as in a second reaction zone. Reduced carbon monoxide concentrations are also encountered in the product recovery section of an acetic acid process. Acetic acid product may be recovered from the second reaction zone and optionally together with or separately from the first reaction zone by flash separation. In flash separation liquid reaction composition is passed to a flashing zone via a flashing valve. The flash separation zone may be an adiabatic flash vessel or may have additional heating means. In the flash separation zone a liquid fraction comprising the majority of the iridium catalyst and the majority of the promoter is separated from a vapour fraction comprising acetic acid, carbonylatable reactant, water and methyl iodide carbonylation co-catalyst and non-condensable gases such as nitrogen, carbon monoxide, hydrogen and carbon dioxide; the liquid fraction being recycled to the first reaction zone and the vapour fraction being passed to one or more distillation zones. In a first distillation zone acetic acid product is separated from the light components (methyl iodide and methyl acetate). The light components are removed overhead, and recycled to the first and/or second reaction zones. Also removed overhead is a low pressure off-gas comprising the non-condensable gases such as nitrogen, carbon monoxide, hydrogen and carbon dioxide. Such a low-pressure off-gas stream may be passed through an off-gas treatment section to remove condensable materials such as methyl iodide, prior to being vented to atmosphere, for example, via a flare.

Where, catalyst system precipitate has already formed, for example, in the second reaction zone and/or in the product recovery section, the precipitate may be dissolved back into solution by the direct and/or indirect addition of the stabilising compound to the reaction zone(s). Optionally, heat, agitation and/or increased carbon monoxide partial pressure may be employed to aid further the re-dissolution of the precipitate.

The present invention also provides a process for the production of acetic acid which process comprises:

a) carbonylating methanol and/or a reactive derivative thereof with carbon monoxide in a first carbonylation reaction zone containing a liquid reaction composition comprising an iridium carbonylation catalyst, methyl iodide co-catalyst, a finite concentration of water, acetic acid, methyl acetate, at least one promoter selected from ruthenium, osmium and rhenium and a stabilising compound selected from the group consisting of alkali metal iodides, alkaline earth metal iodides, metal complexes capable of generating I-, salts capable of generating I-, and mixtures of two or more thereof wherein the molar ratio of promoter to iridium is greater than 2:1, and the molar ratio of stabilising compound to iridium is in the range [greater than 0 to 5]:1 to produce acetic acid, b) withdrawing liquid reaction composition from the reaction zone together with dissolved and/or entrained carbon monoxide, c) optionally passing at least a portion of said withdrawn liquid reaction composition to one or more further reaction zones to consume at least a portion of the dissolved and/or entrained carbon monoxide, d) passing said liquid reaction composition from step (b) and optional step (c) into one or more flash separation stages to form a vapour fraction comprising acetic acid product and a low pressure off-gas comprising carbon monoxide and a liquid fraction comprising iridium carbonylation catalyst, promoter and acetic acid solvent, e) recycling the liquid fraction from the flash separation stage to the reaction zone.

The acetic acid produced by the process according to the present invention may be further purified by conventional processes, for example further distillation to remove impurities such as water, unreacted carbonylation reactant and/or ester derivative thereof and higher-boiling by-products.

The process of the present invention may be performed as a batch or as a continuous process, preferably as a continuous process.

BRIEF DESCRIPTION OF THE DRAWINGS

The present invention will now be illustrated by way of example only and with reference to the following Examples and with reference to FIGS. 1 and 2.

GENERAL EXPERIMENTAL METHOD FOR EXPERIMENTS A AND B AND EXAMPLES 1-7

All experiments were performed in a 300 cm$^3$ zirconium autoclave, equipped with a stirrer and a liquid injection facility. The autoclave was pressure tested to $4 \times 10^6$ N/m$^2$ with nitrogen, then flushed three times with carbon monoxide up to $1 \times 10^6$ N/m$^2$. An initial charge consisting of methyl acetate, acetic acid, methyl iodide, ruthenium acetate solution (5.08% Ru w/w, in acetic acid:water, 4:1), and water was placed into the autoclave, which was then repurged with carbon monoxide and vented slowly to prevent loss of volatiles.

Carbon monoxide (approx $6-7 \times 10^5$ N/m$^2$) was fed into the autoclave which was then heated, with stirring (1500 rpm) to 190° C. The catalyst injection system was primed with approx 5.6 g of iridium acetate solution (5.25% Ir w/w, in acetic acid:water, 4:1) and acetic acid (approx 8.7 g) and injected with an overpressure of carbon monoxide to bring the autoclave pressure to $2.8 \times 10^6$ N/m$^2$ The reaction rate was monitored by drop in carbon monoxide pressure from a ballast vessel, typically pressured to $7 \times 10^6$ N/m$^2$ The autoclave was maintained at a constant temperature of 190° C. and pressure of $2.8 \times 10^6$ N/m$^2$ throughout the reaction. The reaction was terminated when the drop in ballast pressure became less than $1 \times 10^4$ N/m$^2$ per 5 minutes.

After cooling, a gas analysis sample was taken, and the autoclave vented. The liquid components were discharged, and analysed for liquid by-products by known established gas chromatography methods. Detected components are quantified by integration of the component peaks relative to an external standard and expressed as parts per million (ppm) by weight.

In the batch reactions, 'Total' propanoic acid was defined as the sum of propanoic acid and its precursors ((ethyl acetate and ethyl iodide) converted to ppm propanoic acid) detected in the quenched liquid products of the batch reaction expressed in ppm.

The rate of gas uptake at a certain point in a reaction run was used to calculate the carbonylation rate, as number of moles of reactant consumed per liter of cold degassed reactor composition per hour (mol/l/h) at a particular reactor composition (total reactor composition based on a cold degassed volume)

The methyl acetate concentration was calculated during the course of the reaction from the starting composition, assuming that one mole of methyl acetate was consumed for every mole of carbon monoxide that was consumed. No allowance was made for organic components in the autoclave headspace.

EXAMPLES

Experiment A

A baseline experiment was performed with the autoclave charged with methyl acetate (48.05 g) acetic acid (48.42 g) ruthenium acetate solution (12.28 g) water (13.86 g) methyl iodide (13.31 g). The catalyst solution consisted of an iridium solution (5.25% Ir w/w) with acetic acid (8.71 g). The approximate ratio of iridium to ruthenium was 1:4. The rate of reaction, based on carbon monoxide uptake was measured to be 19.6 mol/l/h at a calculated reaction composition of 11% methyl acetate and steadily declined until virtually all the methyl acetate was consumed. Conversion to acetic acid was 99.66% based on methyl acetate consumed. Analysis of propanoic acid precursors gave a total propanoic acid make of 467.8 ppm. Gaseous by-products in the cold-vented off-gas were $H_2$ 3.6 mmol; $CO_2$ 8.0 mmol and $CH_4$ 12.6 mmol. The cooled reaction mixture showed a clearly observable amount of solid material. These results are shown in Table 1.

Example 1

Experiment A was repeated with the autoclave charged with methyl acetate (48.05 g) acetic acid (57.2 g) ruthenium acetate solution (12.2 g) water (13.83 g) methyl iodide (13.34 g) and lithium iodide (0.11 g). The catalyst solution consisted of an iridium solution (5.25% Ir w/w). Conversion to acetic acid was 98.58% based on methyl acetate consumed. No precipitate was observed in the cooled reaction mixture even after several days. The results are shown in Table 1.

Example 2

Experiment A was repeated with the autoclave charged with methyl acetate (48.05 g) acetic acid (57.2 g) ruthenium acetate solution (12.2 g) water (13.83 g) methyl iodide (13.34 g) and lithium iodide (0.0561 g). The catalyst solution consisted of an iridium solution (5.25% Ir w/w). Conversion to acetic acid was 98.94% based on methyl acetate consumed. No precipitate was observed in the cooled reaction mixture even after several days. The results are shown in Table 1.

TABLE 1

| Expt | Ru:Ir | LiI:Ir | Rate mol/ l/h | Precipitate formed | Propanoic acid/ ppm | $H_2$/ mmol | $CO_2$/ mmol | $CH_4$/ mmol |
|---|---|---|---|---|---|---|---|---|
| Expt A | 4:1 | — | 19.6 | Yes | 467.8 | 3.6 | 8.0 | 12.6 |
| Ex 1 | 4:1 | 0.5:1 | 17.9 | No | 296.5 | 3.0 | 8.1 | 13.8 |
| Ex 2 | 4:1 | 0.25:1 | 17.0 | No | 369.0 | 1.7 | 5.5 | 8.5 |

From Table 1 it can be seen that the iodide compound has a significant solubilising effect on the catalyst system and without incurring a significant decrease in carbonylation rate.

Experiment B

A baseline experiment was performed with the autoclave charged with methyl acetate (48.06 g) acetic acid (58.03 g) ruthenium acetate solution (24.35 g) water (12.01 g) methyl iodide (13.30 g). The catalyst solution consisted of an iridium solution (5.25% Ir w/w). The rate of reaction, based on carbon monoxide uptake was measured to be 22.2 mol/l/h at a calculated reaction composition of 11% methyl acetate and steadily declined until virtually all the methyl acetate was consumed. Conversion to acetic acid was 98.80% based on methyl acetate consumed. Analysis of propionic acid precursors gave a total propanoic acid make of 399.7 ppm. The cooled reaction mixture showed a significant amount of clearly visible precipitate. The results are shown in Table 2.

Example 3

Experiment B was repeated with the autoclave charged with methyl acetate (48.14 g) acetic acid (58.08 g) ruthenium acetate solution (24.34 g) water (12.00 g) methyl iodide (13.33 g) and lithium iodide (0.1076 g). Conversion to acetic acid was 98.55% based on methyl acetate consumed. No precipitate was observed in the cooled reaction mixture even after several days. The results are shown in Table 2.

Example 4

Experiment B was repeated with the autoclave charged with methyl acetate (48.13 g) acetic acid (58.02 g) ruthenium acetate solution (24.35 g) water (12.02 g) methyl iodide (13.30 g) and lithium Iodide (0.052 g). The catalyst solution consisted of an iridium solution (5.25% Ir w/w). Conversion to acetic acid was 98.63% based on methyl acetate consumed. No precipitate was observable in the cooled reaction mixture even after several days. The results are given in Table 2.

Example 5

Experiment B was repeated with the autoclave charged with methyl acetate (48.01 g) acetic acid (58.03 g) ruthenium acetate solution (24.34 g) water (12.05 g) methyl iodide (13.34 g) and lithium iodide (0.0333 g). The catalyst solution consisted of an iridium solution (5.25% Ir w/w). Conversion to acetic acid was 98.81% based on methyl acetate consumed. No precipitate was observable in the cooled reaction mixture even after several days. The results are shown in Table 2.

Example 6

Experiment B was repeated with the autoclave charged with methyl acetate (48.04 g) acetic acid (58.03 g) ruthenium acetate solution (24.37 g) water (12.45 g) methyl iodide (13.34 g) and lithium iodide (0.0115 g). The catalyst solution consisted of an iridium solution (5.25% Ir w/w). Conversion to acetic acid was 98.50% based on methyl acetate consumed. The cooled reaction mixture was slightly turbid but no solids were visually detected. The results are shown in Table 2.

Example 7

Experiment B was repeated with the autoclave charged with methyl acetate (48.03 g) acetic acid (46.79 g) ruthenium acetate solution (24.39 g) water (12.51 g) methyl iodide (13.31 g) and magnesium acetate tetrahydrate (0.114 g). The catalyst solution consisted of an iridium solution (5.25% Ir w/w). Conversion to acetic acid was 99.2% based on methyl acetate consumed. The cooled reaction mixture was slightly turbid but no solids were visually detected. The results are shown in Table 2.

TABLE 2

| Expt | Ru:Ir | MI:Ir | Rate mol/l/h | Precipitate formed | Propanoic acid/ppm |
|---|---|---|---|---|---|
| Expt B | 8:1 | — | 22.2 | Yes | 399.7 |
| Example 3 | 8:1 | 0.5:1 | 21.0 | No | 365.5 |
| Example 4 | 8:1 | 0.25:1 | 20.8 | No | 348.6 |
| Example 5 | 8:1 | 0.15:1 | 21.8 | No | 354.4 |
| Example 6 | 8:1 | 0.05:1 | 22.0 | No | 320.9 |
| Example 7 | 8:1 | 0.35:1 | 21.1 | No | 320.0 |

MI = LiI or Mg(acetate)$_2$•4H$_2$O

From Table 2 it can be seen that in Examples 3 to 7 the addition of an iodide compound has a significant stabilising effect on the catalyst system. In addition, there was no significant decrease in reaction rate compared to Experiments A and B in which no stabilizing compound was added. In Example 6, where lithium iodide is used at a Li:Ir molar ratio of 0.05:1 a stabilising effect on the catalyst system is achieved but the effect is less marked than at higher Li:Ir ratios. Example 7 demonstrates that the use of a compound capable of generating an iodide compound in the carbonylation reaction, in this case magnesium acetate, has a significant stabilising effect on the catalyst system.

General Experimental Method for Experiments C to G and Examples 8 to 23

Figure 1:
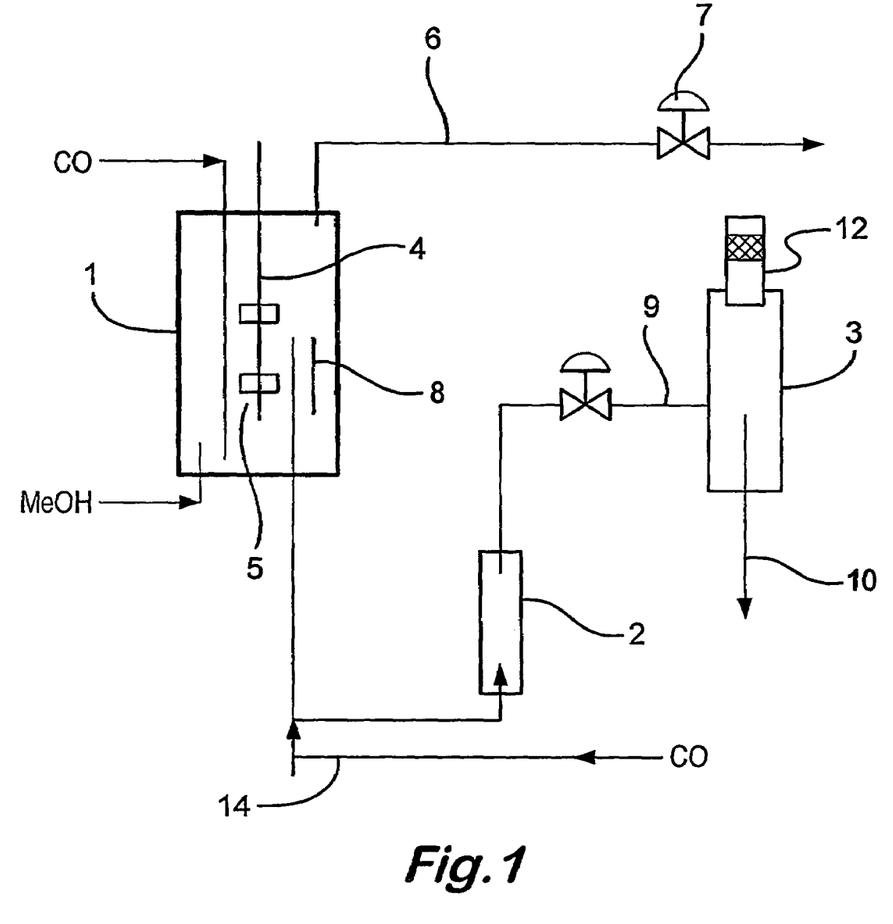
FIG. 1 is a schematic diagram of the apparatus used in the Examples.

The apparatus used is shown in FIG. 1. With reference to FIG. 1 the apparatus comprised a stirred primary carbonylation reactor (1), a secondary carbonylation reactor (2), a flash tank (3) and a distillation column (not shown).

Commercial grade methanol, which has been used to scrub the off-gas was carbonylated in the 6 liter primary reactor (1) in the presence of an iridium carbonylation catalyst and a ruthenium promoter at a pressure of $2.76 \times 10^6$ N/m$^2$ and a temperature of 190° C. The primary reactor (1) was fitted with a stirrer/propeller (4) and a baffle cage (not shown) to ensure intimate mixing of the liquid and gaseous reactants. Carbon monoxide was supplied to the primary reactor (1) via a sparge (5) fitted beneath the stirrer (4). To minimise iron ingress into the primary reactor (1) the carbon monoxide was passed through a carbon filter (not shown). A jacket (not shown), through which the hot oil is circulated, enabled the reaction liquid in the primary reactor (1) to be maintained at a constant reaction temperature. The liquid reaction composition was analysed by near infra-red analysis and gas chromatography. To purge inerts, high pressure off-gas was removed from the primary reactor (1) through line (6). It was passed through a condenser (not shown) before the pressure was dropped across valve (7) and mixed with the low pressure off-gas for it to be fed into the scrubbing system. Liquid reaction composition was withdrawn from the primary reactor (1) down a still well (8), through the secondary reactor (2), and then via line (9) into the flash tank (3) under reactor level control. In the flash tank (3) the liquid reaction composition was flashed down to a pressure of $1.48 \times 10^5$ N/m$^2$. The resulting mixture of vapour and liquid was separated; the catalyst-rich liquid was returned to the primary reactor (1) by line (10) and pump (not shown) and the vapour was passed through a demister (12) and then directly into a distillation column (not shown) as vapour.

The secondary reactor (2) comprised a pipe of diameter 2.5 cm, length 30 cm and together with associated pipework had a volume of approximately 8% of the primary reactor (1). The pipe was placed in parallel to the flashing line (9), and was provided with a supply of additional carbon monoxide via line 14. The secondary reactor (2) was operated at approximately the same pressure as the primary reactor (1).

The vapour from the demister (12) enters the distillation column (not shown) where acetic acid is recovered from the vapour and a low pressure off-gas comprising carbon monoxide is passed to a scrubber (not shown) before being vented.

The degree of catalyst precipitation was measured in conjunction with the liquid reaction composition by near infra red spectroscopy. The increase in the baseline absorbance (measured in absorbance units per day (au/day)) has been found to directly correlate with the amount of precipitation.

Experiment C

Using the apparatus and method as described with reference to FIG. 1, methanol was carbonylated in the primary reactor (1) at a rate of 20 mol/l/h (based on cold degassed reaction volume). The liquid reaction composition in the primary reactor (1) comprised approximately 7% by weight of methyl iodide, 12% by weight of methyl acetate, 5% by weight of water, approx. 76% by weight of acetic acid, 1250 ppm of iridium and 2720 ppm ruthenium. The liquid reaction composition was further carbonylated in the second reactor (2) at a mid temperature of 190° C. and a total pressure of approximately $27 \times 10^5$ N/m$^2$ with a residence time of 40-60 seconds.

Additional carbon monoxide was fed into the secondary reactor to maintain the concentration of carbon monoxide in the non-volatile components exiting the flash tank at 40 mol %. The results are shown in Table 3.

Experiment D

The process of Experiment C was repeated except that no CO was fed into the secondary carbonylation reactor. The results are shown in Table 3. No lithium was added to the carbonylation reactor.

Experiments E to G

The processes of Experiments C and D were repeated except the Ru:Ir ratio in the carbonylation reactor was increased to a molar ratio of 6:1 and the amount of CO fed into the secondary carbonylation reactor was varied. The results are shown in Table 3. No lithium was added to the carbonylation reactor in Experiments E to G.

Examples 8 to 23

The processes of Experiments C to G were repeated except various amounts of lithium were added to the first carbonylation reactor. The results are shown in Table 3.

increased without incurring significant catalyst system precipitation.

Experimental Method for Experiments H and I and Examples 24 to 32

All the experiments were carried out using a Fischer-Porter apparatus comparing a 30 ml glass reaction vessel enclosed by a metal cage and encased with a reinforced cabinet. The single port on the head of the vessel was connected by stainless steel work to a pressure gauge. The apparatus was fitted with a relief valve, a liquid sampling system, a wash port and an inlet manifold. The reaction mixture was agitated by means of a magnetic stirrer bar. The glass reaction vessel was heated by means of immersion in an oil bath.

Experiment H

A known amount of catalyst system precipitate comprising iridium and ruthenium (1.0 g) and a synthesised carbonylation reaction solution (25.0 g) were transferred into the glass reaction vessel of the Fischer Porter apparatus. The apparatus was then assembled and pressure tested for 20 minutes at approx. $6\times10^5$ $N/m^2$. The vessels were then

TABLE 3

| Expt/Ex | Ir (ppm) | Ru:Ir (molar) | LiI:Ir (molar) | [CO] in low pressure off gas (mol %) | Precipitation Rate | CO2 Rate (% carbon) | Propanoic acid/ppm |
|---|---|---|---|---|---|---|---|
| C | 1250 | 4.1 | 0.0 | 40 | −0.003 | 0.9 | 490 |
| D | 1190 | 4.1 | 0.0 | 12 | 0.080 | 0.9 | 520 |
| E | 1160 | 6.0 | 0.0 | 41 | 0.003 | 0.9 | 550 |
| F | 1160 | 5.8 | 0.0 | 20 | 0.072 | 0.9 | 540 |
| G | 1110 | 5.9 | 0.0 | 15 | 0.125 | 0.9 | 570 |
| 8 | 1170 | 6.0 | 0.7 | 41 | 0.001 | 0.8 | 520 |
| 9 | 1150 | 5.9 | 0.7 | 20 | 0.024 | 0.8 | 520 |
| 10 | 1210 | 5.7 | 0.6 | 19 | 0.056 | 0.9 | 550 |
| 11 | 1370 | 4.1 | 0.4 | 40 | 0.003 | 0.9 | 550 |
| 12 | 1400 | 4.0 | 0.4 | 19 | 0.029 | 1.0 | 530 |
| 13 | 1350 | 4.0 | 0.5 | 15 | 0.047 | 0.9 | 540 |
| 14 | 1490 | 4.1 | 0.8 | 40 | −0.001 | 0.9 | 510 |
| 15 | 1500 | 4.0 | 0.7 | 20 | 0.009 | 0.9 | 520 |
| 16 | 1490 | 4.0 | 0.7 | 13 | 0.025 | 0.9 | 530 |
| 17 | 1450 | 5.9 | 1.2 | 40 | 0.000 | 0.9 | 470 |
| 18 | 1430 | 6.0 | 1.1 | 21 | 0.017 | 0.8 | 510 |
| 19 | 1400 | 5.8 | 1.1 | 19 | 0.051 | 0.9 | 490 |
| 20 | 1800 | 5.9 | 2.5 | 41 | 0.000 | 0.9 | 470 |
| 21 | 1670 | 5.7 | 2.5 | 22 | 0.002 | 1.0 | 500 |
| 22 | 1880 | 4.2 | 2.1 | 41 | 0.002 | 0.9 | 470 |
| 23 | 1910 | 4.2 | 2.0 | 19 | 0.000 | 0.9 | 510 |

Figure 2:
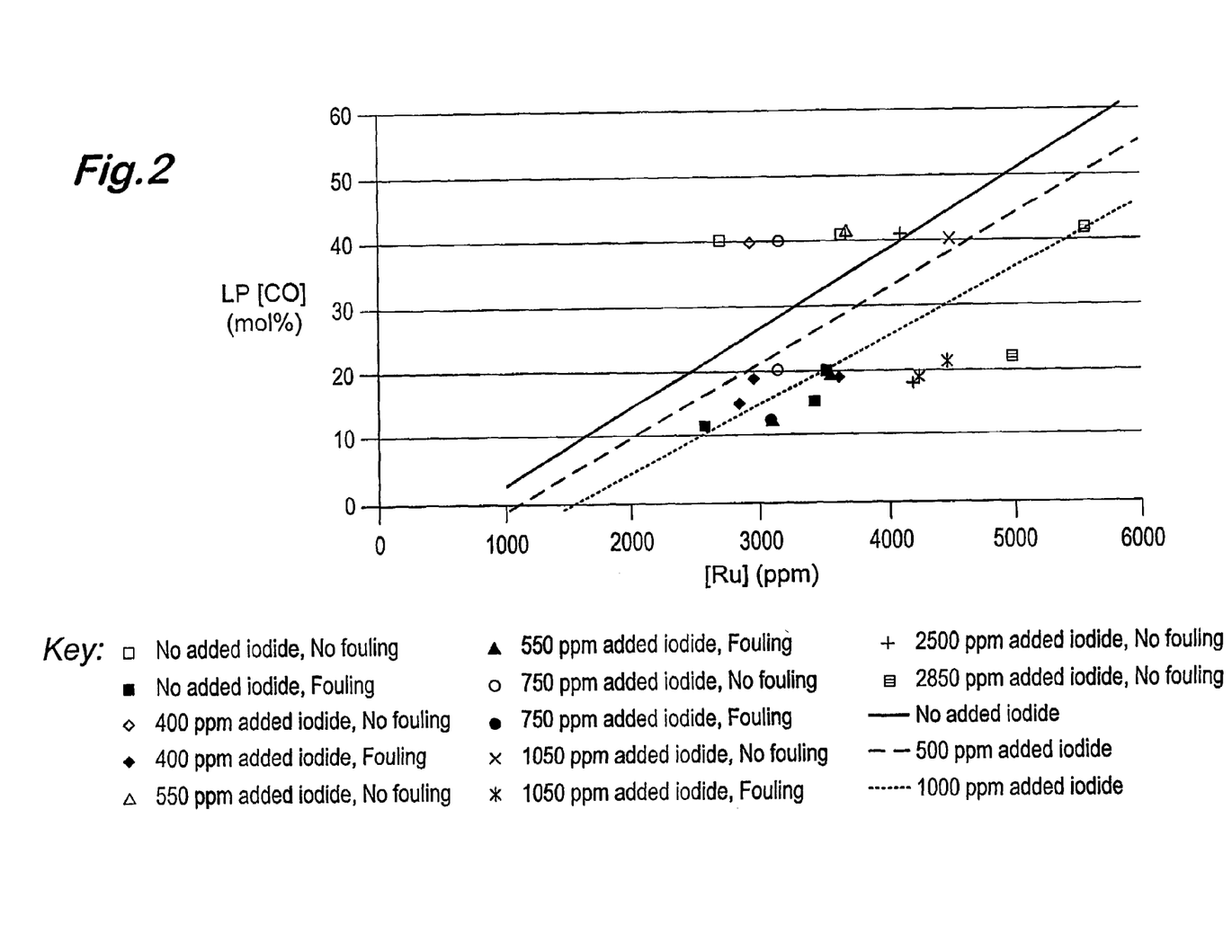
FIG. 2 is a graph of the effects of a stabilising compound on catalyst system stability at varying carbon monoxide concentrations in the low pressure off-gas and ruthenium concentrations.

FIG. 2 illustrates in a graph the stabilizing effect of lithium iodide on a catalyst system at varying low pressure off-gas carbon monoxide concentrations and ruthenium concentrations. The data points in the graph are derived from the results of the Experiments in Table 3 above. Where the fouling rate is greater then 0.001 au/day it has been assumed that solids formation occurs.

As can be seen from the graph, the use of an stabilising compound according to the present invention allows (a) for a given ruthenium concentration, the low pressure off-gas carbon monoxide concentration to be decreased without incurring significant catalyst system precipitation and (b) for a given carbon monoxide concentration in the low pressure off-gas, the concentration of catalyst promoter to be flushed 3 times with nitrogen. The reaction mixture was then heated to temperature (190° C. and 130° C.) for 24 hours under $2\times10^5$ $N/m^2$ of nitrogen. The resulting solution was allowed to cool to less than 30° C., depressurized (if necessary) and centrifuged at 4400 rpm for 5 minutes. A sample of the resulting solution was analysed by X-Ray Fluorescence (XRF) for iridium and ruthenium concentration. The composition of the synthesised carbonylation reaction solution is given in Table 4. The results of the experiment are given in Table 5.

Experiment I

Experiment H was repeated except that a synthesised catalyst recycle solution (CRS) was used in place of a synthesized carbonylation reaction solution. The composition of the synthesised catalyst recycle solution is given in Table 4. The results of the experiment are given in Table 6.

TABLE 4

| | Composition (g) | | Composition (cm³) | | % w/w | |
|---|---|---|---|---|---|---|
| | Reaction Solution | CRS | Reaction Solution | CRS | Reaction Solution | CRS |
| MeOAc | 63.15 | 46.25 | 67.75 | 49.62 | 12.00 | 9.00 |
| AcOH | 400.00 | 440.00 | 318.316 | 419.44 | 76.00 | 85.60 |
| H₂O | 26.30 | 20.55 | 26.30 | 20.55 | 5.00 | 4.00 |
| MeI | 36.85 | 7.20 | 16.16 | 3.15 | 7.00 | 1.40 |

Examples 24 to 26

Experiment H was repeated except that prior to the addition of the synthesised carbonylation reaction solution to the Fischer Porter apparatus, an amount of lithium iodide was added to the solution. The results of the experiments are given in Table 5.

TABLE 5

| | Amount of LiI added to the synthesised reaction solution (g) | Final Ir concentration (ppm) | Final Ru concentration (ppm) |
|---|---|---|---|
| Experiment H | 0 | 170 | 830 |
| Example 24 | 0.02 | 170 | 900 |
| Example 25 | 0.03 | 250 | 1230 |
| Example 26 | 0.05 | 500 | 2310 |

Examples 27 to 29

Experiment I was repeated except that prior to the addition of the synthesised catalyst recycle solution to the Fischer Porter apparatus, an amount of lithium iodide was added to the solution. The results of the experiments are given in Table 6.

TABLE 6

| | Amount of LiI added to the synthesised CRS (g) | Final Ir concentration (ppm) | Final Ru concentration (ppm) |
|---|---|---|---|
| Experiment I | 0 | 120 | 550 |
| Example 27 | 0.02 | 310 | 1260 |
| Example 28 | 0.02 | 300 | 1280 |
| Example 29 | 0.05 | 570 | 2290 |

From an inspection of Tables 4 and 5 it can be seen that the addition of lithium iodide to the carbonylation and catalyst recycle solutions aids in the redissolution of catalyst system precipitate in both the carbonylation reaction (Table 4) and catalyst recycle solutions (Table 5).

Examples 30 to 32

Experiment I was repeated except that prior to the addition of the synthesised catalyst recycle solution to the Fischer Porter apparatus, an amount of an iodide stabilizing compound was added to the solution. Details of the stabilizing compound added are given in Table 7. The results of the experiments are also given in Table 7.

TABLE 7

| | Stabilising compound | Mass of stabilising compound added (g) | Final Ir concentration (ppm) | Final Ru concentration (ppm) |
|---|---|---|---|---|
| Example 30 | Sodium Iodide | 0.03 | 350 | 1400 |
| Example 31 | Potassium Iodide | 0.03 | 400 | 1600 |
| Example 32 | Molybdenum (II) Iodide | 0.07 | 200 | 850 |

A comparison of Examples 30 to 32 with Experiment I demonstrates that □tabilizing compounds other than lithium iodide can also assist the solubilisation of catalyst system precipitate

The invention claimed is:

1. A process for the production of acetic acid comprising carbonylating methanol and/or a reactive derivative thereof with carbon monoxide in a carbonylation reaction zone containing a liquid reaction composition comprising an iridium carbonylation catalyst, methyl iodide co-catalyst, a finite concentration of water, acetic acid, methyl acetate, at least one promoter selected from the group consisting of ruthenium, osmium and rhenium and a stabilizing compound selected from the group consisting of alkali metal iodides, alkaline earth metal iodides, metal complexes capable of generating I⁻, salts capable of generating I⁻, and mixtures of two or more thereof wherein the molar ratio of promoter to iridium is greater than 2:1, and the molar ratio of stabilizing compound to iridium is in the range greater than 0:1 to 5:1, except that when the stabilizing compound is a lithium compound the molar ratio of promoter to iridium is greater than 5:1 and the molar ratio of the lithium stabilizing compound to iridium is 0.05:1 to 5:1, such that loss of the catalyst and/or the promoter from the liquid reaction composition and/or subsequent process streams is reduced.

2. A process according to claim 1 wherein the process comprises the further steps of:
    (a) withdrawing liquid reaction composition together with dissolved and/or entrained carbon monoxide and other gases from said carbonylation reaction zone;
    (b) optionally passing said withdrawn liquid reaction composition through one or more further reaction zones to consume at least a portion of the dissolved and/or entrained carbon monoxide;
    (c) passing said composition from step (a) and optional step (b) into one or more flash separation stages to form (i) a vapour fraction comprising condensable components and low pressure off-gas, the condensable components comprising acetic acid product and the low pressure off-gas comprising carbon monoxide and other gases dissolved and/or entrained with the withdrawn liquid carbonylation reaction composition and (ii) a liquid fraction comprising iridium carbonylation catalyst, promoter and acetic acid solvent;
    (d) separating the condensable components from the low pressure off-gas; and
    (e) recycling the liquid fraction from the flash separation stage to the carbonylation reactor.

3. A process according to claim 1 wherein the molar ratio of promoter:iridium is in the range greater than 2:1 to 15:1 and the stabilizing compound is not a lithium stabilizing compound.

4. A process according to claim 1 wherein the molar ratio of promoter:iridium is in the range greater than 2:1 to 5:1.

5. A process according to claim 3 wherein the molar ratio of promoter:iridium is in the range 4:1 to 10:1 and the stabilizing compound is not a lithium stabilizing compound.

6. A process according to claim 3 wherein the molar ratio of promoter:iridium is in the range 6:1 to 12:1.

7. A process according to claim 3 wherein the molar ratio of stabilizing compound:iridium is in the range 0.05:1 to 3:1.

8. A process according to claim 4 wherein the molar ratio of stabilizing compound:iridium is in the range 0.05:1 to 3:1.

9. A process according to claim 7 wherein the molar ratio of stabilizing compound:iridium is in the range 0.05:1 to 1.5:1.

10. A process according to claim 8 wherein the molar ratio of stabilizing compound:iridium is in the range 0.05:1 to 1.5:1.

11. A process according to claim 5 wherein the molar ratio of stabilizing compound:iridium is in the range 0.15:1 to 2.5:1.

12. A process according to claim 6 wherein the molar ratio of stabilizing the compound:iridium is in the range 0.15:1 to 2.5:1.

13. A process according to claim 11 wherein the molar ratio of stabilizing compound:iridium is in the range 0.15:1 to 2:1.

14. A process according to claim 12 wherein the molar ratio of stabilizing compound:iridium is in the range 0.15:1 to 2:1.

15. A process according to claim 1 wherein the stabilizing compound is selected from the group consisting of alkali metal iodide, alkaline earth metal iodide, alkali metal salts capable of generating iodide ions and alkaline earth metal salts capable of generating iodide ions.

16. A process according to claim 15 wherein the stabilizing compound is an alkali metal iodide or an alkali metal salt capable of generating iodide ions.

17. A process according to claim 16 wherein the stabilizing compound is selected from the group consisting of lithium iodide, lithium acetate, sodium iodide and sodium acetate.

18. A process according to claim 1 wherein the stabilizing compound is introduced directly into the reaction zone or is introduced indirectly into a reaction zone.

19. A process according to claim 18 wherein the stabilizing compound is introduced into the reaction zone via a recycle stream.

20. A process according to claim 19 wherein the recycle stream is a catalyst recycle stream.

21. A process according to claim 2, wherein the stabilizing compound is added to the one or more further reaction zones.

22. A process according to claim 2, wherein the stabilizing compound is added to the liquid fraction from the flash separation stage.

* * * * *